United States Patent
Lawes et al.

(10) Patent No.: US 7,135,020 B2
(45) Date of Patent: *Nov. 14, 2006

(54) ELECTROSURGICAL INSTRUMENT REDUCING FLASHOVER

(75) Inventors: Kate R. Lawes, Superior, CO (US); Sean T. Dycus, Denver, CO (US); Kristin D. Johnson, Louisville, CO (US); Philip M. Tetzlaff, Superior, CO (US); Steven P. Buysse, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 110 days.

This patent is subject to a terminal disclaimer.

(21) Appl. No.: 10/474,226

(22) PCT Filed: Apr. 6, 2001

(86) PCT No.: PCT/US01/11411

§ 371 (c)(1),
(2), (4) Date: Oct. 3, 2003

(87) PCT Pub. No.: WO02/080785

PCT Pub. Date: Oct. 17, 2002

(65) Prior Publication Data

US 2004/0176762 A1 Sep. 9, 2004

Related U.S. Application Data

(63) Continuation-in-part of application No. 09/387,883, filed on Sep. 1, 1999, now abandoned, which is a continuation of application No. 08/968,496, filed on Nov. 12, 1997, now Pat. No. 6,050,996.

(51) Int. Cl.
*A61B 18/18* (2006.01)

(52) U.S. Cl. .......................................... 606/51; 606/50
(58) Field of Classification Search ............ 606/45–52, 606/205–208
See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2104423 | 2/1994 |

(Continued)

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC, 2003.

(Continued)

Primary Examiner—Michael Peffley

(57) ABSTRACT

An electrode assembly for use in combination with an electrosurgical instrument which includes opposing end effectors and a handle for effecting movement of the end effectors relative to one another. The assembly includes a housing having one portion which is removably engageable with the electrosurgical instrument and a pair of electrodes each having an electrically conductive sealing surface and an insulating substrate. The electrodes are removably engageable with the end effectors of the electrosurgical instrument such that the electrodes reside in opposing relation relative to one another. The insulating substrate is made from a plastic material having a high Comparative Tracking Index to reduce the incidence of flashover.

18 Claims, 10 Drawing Sheets

U.S. PATENT DOCUMENTS

| | | |
|---|---|---|
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A * | 8/1988 | Jaeger .................. 600/564 |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A * | 2/1995 | Tsuruta et al. ................ 606/41 |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Kipshidze et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A * | 3/1996 | Hashiguchi et al. ........ 606/205 |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |

| | | | | | |
|---|---|---|---|---|---|
| 5,649,959 A | 7/1997 | Hannam et al. | 6,083,223 A | 7/2000 | Baker |
| 5,658,281 A | 8/1997 | Heard | 6,086,586 A * | 7/2000 | Hooven ..................... 606/50 |
| 5,662,667 A | 9/1997 | Knodel | 6,090,107 A | 7/2000 | Borgmeier et al. |
| 5,667,526 A | 9/1997 | Levin | 6,096,031 A | 8/2000 | Mitchell et al. |
| 5,674,220 A | 10/1997 | Fox et al. | 6,096,037 A | 8/2000 | Mulier et al. |
| 5,681,282 A | 10/1997 | Eggers et al. | 6,099,550 A | 8/2000 | Yoon |
| 5,693,051 A | 12/1997 | Schulze et al. | 6,102,909 A | 8/2000 | Chen et al. |
| 5,695,522 A | 12/1997 | LeMaire, III et al. | 6,110,171 A | 8/2000 | Rydell |
| 5,700,261 A | 12/1997 | Brinkerhoff | 6,113,596 A | 9/2000 | Hooven et al. |
| 5,702,390 A | 12/1997 | Austin et al. | 6,113,598 A | 9/2000 | Baker |
| 5,707,369 A | 1/1998 | Vaitekunas et al. | 6,117,158 A | 9/2000 | Measamer et al. |
| 5,709,680 A | 1/1998 | Yates et al. | H1904 H | 10/2000 | Yates et al. |
| 5,716,366 A | 2/1998 | Yates | 6,126,658 A | 10/2000 | Baker |
| 5,727,428 A | 3/1998 | LeMaire, III et al. | 6,152,923 A | 11/2000 | Ryan |
| 5,735,848 A | 4/1998 | Yates et al. | 6,174,309 B1 | 1/2001 | Wrublewski et al. |
| 5,743,906 A * | 4/1998 | Parins et al. .................. 606/51 | 6,179,834 B1 | 1/2001 | Buysse et al. |
| 5,755,717 A | 5/1998 | Yates et al. | 6,179,837 B1 | 1/2001 | Hooven |
| 5,766,130 A | 6/1998 | Selmonosky | 6,183,467 B1 | 2/2001 | Shapeton et al. |
| 5,766,166 A | 6/1998 | Hooven | 6,187,003 B1 | 2/2001 | Buysse et al. |
| 5,766,170 A | 6/1998 | Eggers | 6,190,386 B1 | 2/2001 | Rydell |
| 5,769,849 A | 6/1998 | Eggers | 6,193,718 B1 | 2/2001 | Kortenbach et al. |
| 5,776,128 A | 7/1998 | Eggers | 6,206,876 B1 | 3/2001 | Levine et al. |
| 5,776,130 A | 7/1998 | Buysse et al. | 6,206,877 B1 | 3/2001 | Kese et al. |
| 5,779,701 A | 7/1998 | McBrayer et al. | 6,224,593 B1 | 5/2001 | Ryan et al. |
| 5,792,137 A | 8/1998 | Carr et al. | 6,228,080 B1 | 5/2001 | Gines |
| 5,792,177 A | 8/1998 | Kaseda | 6,228,083 B1 | 5/2001 | Lands et al. |
| 5,797,938 A | 8/1998 | Paraschac et al. | 6,267,761 B1 | 7/2001 | Ryan |
| 5,797,958 A | 8/1998 | Yoon | 6,270,497 B1 | 8/2001 | Sekino et al. |
| 5,800,449 A | 9/1998 | Wales | 6,270,508 B1 | 8/2001 | Klieman et al. |
| 5,810,808 A | 9/1998 | Eggers | 6,273,887 B1 | 8/2001 | Yamauchi et al. |
| 5,810,811 A | 9/1998 | Yates et al. | 6,277,117 B1 | 8/2001 | Tetzlaff et al. |
| 5,810,877 A | 9/1998 | Roth et al. | 6,280,458 B1 | 8/2001 | Boche et al. |
| 5,814,043 A | 9/1998 | Shapeton | 6,283,961 B1 | 9/2001 | Underwood et al. |
| 5,820,630 A | 10/1998 | Lind | D449,886 S | 10/2001 | Tetzlaff et al. |
| 5,827,271 A | 10/1998 | Buysse et al. | 6,322,561 B1 | 11/2001 | Eggers et al. |
| 5,827,279 A | 10/1998 | Hughett et al. | 6,334,860 B1 | 1/2002 | Dorn |
| 5,827,281 A | 10/1998 | Levin | 6,334,861 B1 | 1/2002 | Chandler et al. |
| 5,833,690 A | 11/1998 | Yates et al. | 6,350,264 B1 | 2/2002 | Hooven |
| 5,843,080 A | 12/1998 | Fleenor et al. | 6,352,536 B1 | 3/2002 | Buysse et al. |
| 5,849,022 A | 12/1998 | Sakashita et al. | D457,958 S | 5/2002 | Dycus et al. |
| 5,853,412 A | 12/1998 | Mayenberger | D457,959 S | 5/2002 | Tetzlaff et al. |
| 5,876,401 A | 3/1999 | Schulze et al. | 6,387,094 B1 | 5/2002 | Eitenmuller |
| 5,891,141 A | 4/1999 | Rydell | 6,398,779 B1 | 6/2002 | Buysse et al. |
| 5,891,142 A | 4/1999 | Eggers et al. | 6,402,747 B1 | 6/2002 | Lindemann et al. |
| 5,893,863 A | 4/1999 | Yoon | 6,409,728 B1 | 6/2002 | Ehr et al. |
| 5,893,875 A | 4/1999 | O'Connor et al. | H2037 H | 7/2002 | Yates et al. |
| 5,893,877 A | 4/1999 | Gampp, Jr. et al. | 6,419,675 B1 | 7/2002 | Gallo, Sr. |
| 5,902,301 A | 5/1999 | Olig | 6,425,896 B1 | 7/2002 | Baltschun et al. |
| 5,906,630 A | 5/1999 | Anderhub et al. | 6,443,970 B1 | 9/2002 | Schulze et al. |
| 5,908,420 A | 6/1999 | Parins et al. | 6,451,018 B1 | 9/2002 | Lands et al. |
| 5,913,874 A | 6/1999 | Berns et al. | 6,458,128 B1 | 10/2002 | Schulze |
| 5,921,984 A | 7/1999 | Sutcu et al. | 6,458,130 B1 | 10/2002 | Frazier et al. |
| 5,935,126 A | 8/1999 | Riza | 6,464,704 B1 | 10/2002 | Schmaltz et al. |
| 5,944,718 A | 8/1999 | Dafforn et al. | 6,503,248 B1 | 1/2003 | Levine |
| 5,951,549 A | 9/1999 | Richardson et al. | 6,506,189 B1 | 1/2003 | Rittman, III et al. |
| 5,954,720 A | 9/1999 | Wilson et al. | 6,511,480 B1 | 1/2003 | Tetzlaff et al. |
| 5,961,514 A | 10/1999 | Long et al. | 6,514,251 B1 | 2/2003 | Ni et al. |
| 5,976,132 A | 11/1999 | Morris | 6,544,264 B1 | 4/2003 | Levine et al. |
| 5,984,939 A | 11/1999 | Yoon | 6,569,162 B1 | 5/2003 | He |
| 5,989,277 A | 11/1999 | LeMaire, III et al. | 6,585,735 B1 | 7/2003 | Frazier et al. |
| 6,004,335 A | 12/1999 | Vaitekunas et al. | 6,620,161 B1 | 9/2003 | Schulze et al. |
| 6,010,516 A | 1/2000 | Hulka et al. | 6,652,521 B1 | 11/2003 | Schulze |
| 6,024,741 A | 2/2000 | Williamson et al. | 6,682,528 B1 | 1/2004 | Frazier et al. |
| 6,024,744 A * | 2/2000 | Kese et al. .................. 606/51 | 6,685,724 B1 | 2/2004 | Haluck |
| 6,033,399 A | 3/2000 | Gines | 6,733,498 B1 | 5/2004 | Paton et al. |
| 6,039,733 A | 3/2000 | Buysse et al. | 6,743,229 B1 | 6/2004 | Buysse et al. |
| 6,041,679 A | 3/2000 | Slater et al. | D496,997 S | 10/2004 | Dycus et al. |
| 6,050,996 A | 4/2000 | Schmaltz et al. | D499,181 S | 11/2004 | Dycus et al. |
| 6,053,914 A | 4/2000 | Eggers et al. | 6,926,716 B1 | 8/2005 | Baker et al. |
| 6,053,933 A | 4/2000 | Balazs et al. | 6,929,644 B1 | 8/2005 | Truckai et al. |
| D424,694 S | 5/2000 | Tetzlaff et al. | 6,942,662 B2 | 9/2005 | Goble et al. |
| D425,201 S | 5/2000 | Tetzlaff et al. | 2002/0013583 A1 | 1/2002 | Camran et al. |
| RE36,795 E | 7/2000 | Rydell | 2002/0099372 A1 | 7/2002 | Schulze et al. |

| | | | | | | |
|---|---|---|---|---|---|---|
| 2002/0107517 A1 | 8/2002 | Witt et al. | | EP | 1053719 A1 | 11/2000 |
| 2002/0111624 A1 | 8/2002 | Witt et al. | | EP | 1053720 A1 | 11/2000 |
| 2002/0188294 A1 | 12/2002 | Couture et al. | | EP | 1055399 A1 | 11/2000 |
| 2003/0018331 A1 | 1/2003 | Dycus et al. | | EP | 1055400 A1 | 11/2000 |
| 2003/0069571 A1 | 4/2003 | Treat et al. | | EP | 1080694 A1 | 3/2001 |
| 2003/0078578 A1 | 4/2003 | Truckai et al. | | EP | 1082944 A1 | 3/2001 |
| 2003/0139741 A1 | 7/2003 | Goble et al. | | EP | 1159926 A2 | 12/2001 |
| 2003/0139742 A1 | 7/2003 | Wampler et al. | | EP | 1330991 A1 | 7/2003 |
| 2003/0158549 A1 | 8/2003 | Swanson | | EP | 1488177 A2 | 6/2004 |
| 2003/0199869 A1 | 10/2003 | Johnson et al. | | EP | 1532932 A1 | 5/2005 |
| 2003/0220637 A1 | 11/2003 | Truckai et al. | | GB | 2214430 A | 6/1989 |
| 2003/0236325 A1 | 12/2003 | Bonora | | JP | 501068 | 9/1984 |
| 2004/0049185 A1 | 3/2004 | Latterell et al. | | JP | 502328 | 3/1992 |
| 2004/0116979 A1 | 6/2004 | Truckai et al. | | JP | 5-40112 | 2/1993 |
| 2004/0147925 A1 | 7/2004 | Buysse et al. | | JP | 06343644 A2 | 12/1994 |
| 2004/0225288 A1 | 11/2004 | Buysse et al. | | JP | 07265328 A2 | 10/1995 |
| 2004/0230189 A1 | 11/2004 | Keppel | | JP | 08056955 A2 | 3/1996 |
| 2004/0236325 A1 | 11/2004 | Tetzlaff et al. | | JP | 08252263 A2 | 10/1996 |
| 2004/0243125 A1 | 12/2004 | Dycus et al. | | JP | 09010223 A2 | 1/1997 |
| 2004/0249371 A1 | 12/2004 | Dycus et al. | | JP | 11244298 A2 | 9/1999 |
| 2004/0249374 A1 | 12/2004 | Tetzlaff et al. | | JP | 2000342599 A2 | 12/2000 |
| 2004/0250419 A1 | 12/2004 | Sremcich et al. | | JP | 2000350732 A2 | 12/2000 |
| 2004/0254573 A1 | 12/2004 | Dycus et al. | | JP | 2001008944 A2 | 1/2001 |
| 2005/0004564 A1 | 1/2005 | Wham et al. | | JP | 2001029356 A2 | 2/2001 |
| 2005/0004568 A1 | 1/2005 | Lawes et al. | | JP | 2001128990 A2 | 5/2001 |
| 2005/0004570 A1 | 1/2005 | Chapman et al. | | SU | 401367 | 11/1974 |
| 2005/0021025 A1 | 1/2005 | Buysse et al. | | WO | WO 92/06642 | 4/1992 |
| 2005/0021026 A1 | 1/2005 | Baily | | WO | WO 94/08524 A | 4/1994 |
| 2005/0021027 A1 | 1/2005 | Shields et al. | | WO | WO 95/02369 | 1/1995 |
| 2005/0033278 A1 | 2/2005 | McClurken et al. | | WO | WO 95/07662 | 3/1995 |
| 2005/0101951 A1 | 5/2005 | Wham et al. | | WO | WO 96/022056 | 7/1996 |
| 2005/0101952 A1 | 5/2005 | Lands et al. | | WO | WO 96/13218 | 9/1996 |
| 2005/0107784 A1 | 5/2005 | Moses et al. | | WO | WO 97/00646 | 1/1997 |
| 2005/0107785 A1 | 5/2005 | Dycus et al. | | WO | WO 97/00647 | 1/1997 |
| 2005/0113818 A1 | 5/2005 | Sartor et al. | | WO | WO 97/10764 | 3/1997 |
| 2005/0113819 A1 | 5/2005 | Wham et al. | | WO | WO 97/24073 | 7/1997 |
| 2005/0113826 A1 | 5/2005 | Johnson et al. | | WO | WO 97/24993 | 7/1997 |
| 2005/0113827 A1 | 5/2005 | Dumbauld et al. | | WO | WO 98/27880 | 7/1998 |
| 2005/0113828 A1 | 5/2005 | Shields et al. | | WO | WO 99/03407 | 1/1999 |
| 2005/0119655 A1 | 6/2005 | Moses et al. | | WO | WO 99/03408 | 1/1999 |
| 2005/0149151 A1 | 7/2005 | Orszulak et al. | | WO | WO 99/03409 | 1/1999 |
| 2006/0079891 A1 | 4/2006 | Arts et al. | | WO | WO 99/12488 A | 3/1999 |
| | | | | WO | WO 99/40857 | 8/1999 |
| | FOREIGN PATENT DOCUMENTS | | | WO | WO 99/040881 | 8/1999 |
| | | | | WO | WO 99/51158 | 10/1999 |
| DE | 2415263 | 10/1975 | | WO | WO 99/066850 | 12/1999 |
| DE | 8712328 | 3/1988 | | WO | WO 99/66850 A | 12/1999 |
| DE | 29616210 | 1/1997 | | WO | WO 00/24330 | 5/2000 |
| DE | 19608716 | 4/1997 | | WO | WO 00/24331 | 5/2000 |
| DE | 19751108 | 5/1999 | | WO | WO 00/41638 | 7/2000 |
| EP | 0364216 A1 | 4/1990 | | WO | WO 00/53112 | 9/2000 |
| EP | 518230 A1 | 12/1992 | | WO | WO 01/17448 A | 3/2001 |
| EP | 0 541 930 B1 | 5/1993 | | WO | WO 01/54604 | 8/2001 |
| EP | 0572131 | 12/1993 | | WO | WO 01/54604 A1 | 8/2001 |
| EP | 0572131 A1 | 12/1993 | | WO | WO 02/07627 | 1/2002 |
| EP | 584787 A1 | 3/1994 | | WO | WO 02/080783 | 10/2002 |
| EP | 0623316 A1 | 11/1994 | | WO | WO 02/080784 | 10/2002 |
| EP | 0624348 A2 | 11/1994 | | WO | WO 02/080785 | 10/2002 |
| EP | 0650701 A1 | 5/1995 | | WO | WO 02/080786 | 10/2002 |
| EP | 0694290 A3 | 3/1996 | | WO | WO 02/080793 | 10/2002 |
| EP | 0717966 A1 | 6/1996 | | WO | WO 02/080794 | 10/2002 |
| EP | 0754437 A3 | 3/1997 | | WO | WO 02/080795 | 10/2002 |
| EP | 853922 A1 | 7/1998 | | WO | WO 02/080796 A1 | 10/2002 |
| EP | 0875209 A1 | 11/1998 | | WO | WO 02/080797 | 10/2002 |
| EP | 0878169 A1 | 11/1998 | | WO | WO 02/080798 | 10/2002 |
| EP | 0887046 A3 | 1/1999 | | WO | WO 02/080799 | 10/2002 |
| EP | 0923907 A1 | 6/1999 | | WO | WO 02/081170 | 10/2002 |
| EP | 0988990 A1 | 3/2000 | | WO | WO 03/101311 | 12/2003 |
| EP | 1034747 A1 | 9/2000 | | WO | WO 04/032777 | 4/2004 |
| EP | 1034748 A1 | 9/2000 | | WO | WO 2004/052221 A1 | 6/2004 |
| EP | 1025807 A3 | 10/2000 | | WO | WO 04/073490 | 9/2004 |
| EP | 1034746 A3 | 10/2000 | | WO | WO 2004/082495 A1 | 9/2004 |
| EP | 1050278 A1 | 11/2000 | | WO | WO 04082495 | 9/2004 |

| | | | |
|---|---|---|---|
| WO | WO 2004/098383 A1 | 11/2004 | |
| WO | WO 04/103156 | 12/2004 | |

OTHER PUBLICATIONS

"Reducing Needlestick Injuries in the Operating Room" Sales/Product Literature, 2001.
Chung et al., "Clinical Experience of Suturless Closed Hemorrholdectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Divison During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature, 1999.
Michael Choti, "Abdominoperineal Resection with the LigaSure Vessel Sealing System and LigaSure Atlas 20 cm Open Instrument".
Craig Johnson, "Use of the LigaSure Vessel Sealing System in Bloodless Hemorrhoidectomy" Innovations That Work, Mar. 2000.
Mullar et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vesssel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gyneacology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales Product Literature, 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
E. David Crawford "Use of a Novel Vessel Sealing Technology in Management of the Dorsal Veinous Complex" Sales Product Literature, 2000.
Jarrett et al., "Use of the LigaSure Vessel Sealing System for Peri-Hilar Vessels in Laparoscopic Nephrectomy" Sales Product Literature, 2000.
E. David Crawford "Evaluation of a New Vessel Sealing Device in Urologic Cancer Surgery" Sales Product Literature, 2000.
Joseph Ortenberg "LigaSure System Used in Laparoscopic 1st and 2nd Stage Orchipexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-876.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA. Feb. 2001.
Johnson et al. "Evaluation of the LigaSure Vessel Sealing System in Hemorrhoidectomy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Inital Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l. Federation of Gynecology and Obstetrics FIGO World Congress 2000, Washington, D.C.
Levy et al. "Use of a New Energy-based Vessel Ligation Device During Vaginal Hysterectomy" Int'l. Federation of Gynecology and Obstetrics (FIGO) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al, "Randomized clinical trial of Ligasure versus open haemorrhoidectomy" British Journal of Surgery 2002, 89, 154-157.
Int'l Search Report PCT/US01/11218.
Int'l Search Report PCT/US99/24869.
Int'l Search Report PCT/US98/18640.
Int'l Search Report PCT/US98/23950.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan., 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature: Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2005.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
PCT/US01/11340, International Search Report.
PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report
EP 04027705, International Search Report.
EP 04027314, International Search Report.
US 6,090,109, 07/2000, Lands et al. (withdrawn)
US 6,663,629, 12/2003, Buysse et al. (withdrawn)

* cited by examiner

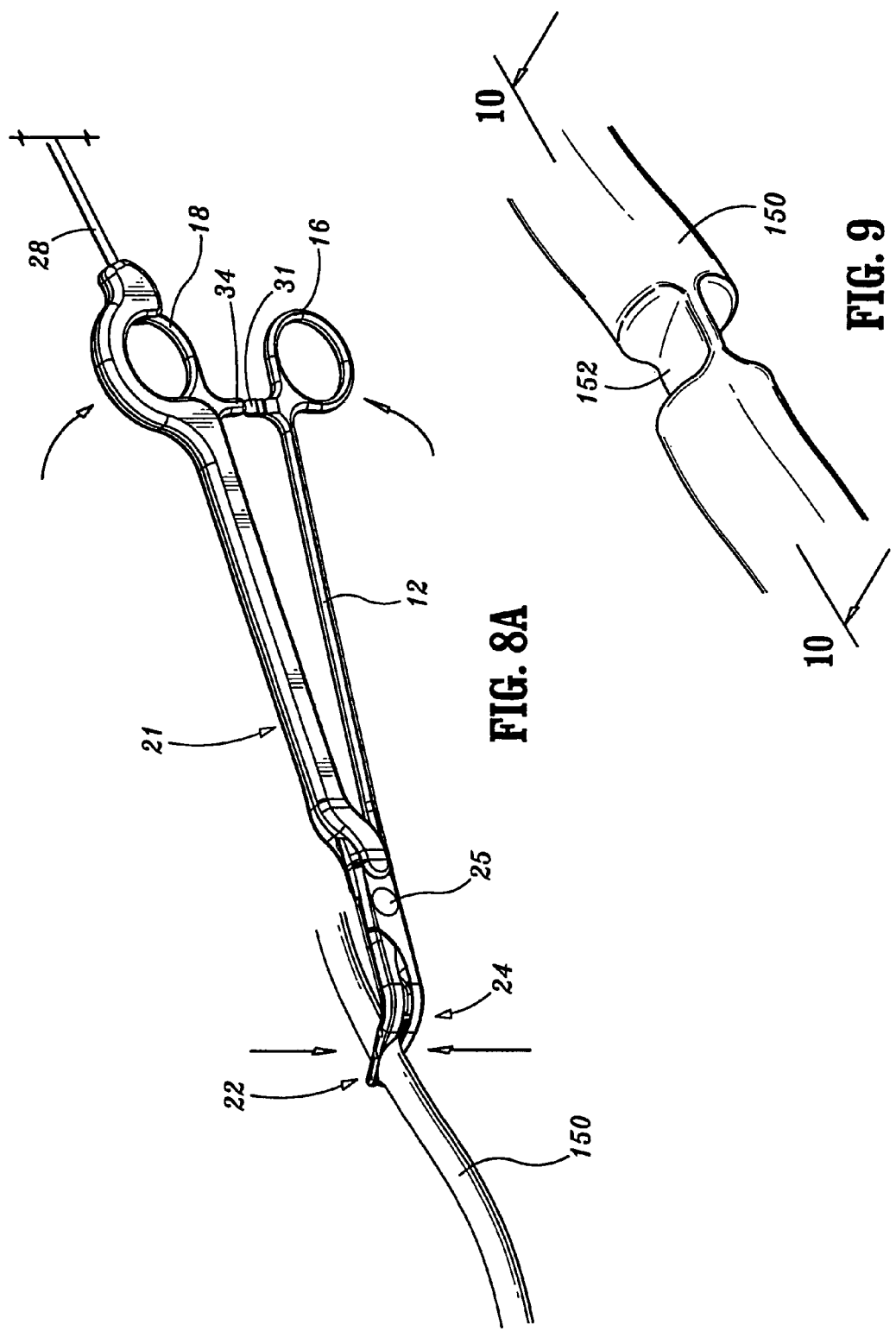

ELECTROSURGICAL INSTRUMENT REDUCING FLASHOVER

CROSS REFERENCE TO RELATED APPLICATION

This application is a continuation-in-part of U.S. application Ser. No. 09/387,883 filed on Sep. 1, 1999, now abandoned which is a continuation of U.S. application Ser. No. 08/968,496, now U.S. Pat. No. 6,050,996 filed on Nov. 12, 1997 the contents of which are hereby incorporated by reference in their entirety.

BACKGROUND

The present disclosure relates to electrosurgical instruments used for open and endoscopic surgical procedures. More particularly, the present disclosure relates to a bipolar forceps for sealing vessels and vascular tissue having an electrode assembly which is designed to reduce the incidence of flashover.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate tissue and/or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are generally disposed on the inner facing or opposing surfaces of the end effectors which, in turn, are electrically coupled to an electrosurgical generator. Each electrode is charged to a different electric potential. Since tissue is a conductor of electrical energy, when the end effectors are utilized to clamp or grasp tissue therebetween, the electrical energy can be selectively transferred through the tissue.

Over the last several decades, more and more surgeons are complimenting traditional open methods of gaining access to vital organs and body cavities with endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

Certain surgical procedures require sealing blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

It is known that the process of coagulating small vessels is fundamentally different than vessel sealing. For the purposes herein the term "coagulation" is defined as a process of desiccating tissue wherein the tissue cells are ruptured and dried. The term "vessel sealing" is defined as the process of liquefying the collagen in the tissue so that the tissue crosslinks and reforms into a fused mass. Thus, coagulation of small vessels is sufficient to close them, however, larger vessels need to be sealed to assure permanent closure.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187–190, describes a method for terminating electrosurgical power to the vessel so that charring of the vessel walls can be avoided.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical instruments have been proposed in the past for various open and endoscopic surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, sealing and cutting vessels or tissue.

Many of these instruments include blade members or shearing members which simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles which may ultimately effect the quality and consistency of the seal and cause socalled "flashover." Flashover as used herein relates to a visual anomaly which develops as a result of inconsistent current tracking over the surface of the insulator or insulative coating and/or activation irregularities which may occur when the instrument is repeatedly used during surgery. Although flashover tends to char the surface of the insulate, it does not effect seal quality. However, it may effect the life of the instrument and/or the electrode assembly. The effects and industry standards with respect to flashover are discussed in detail in the *Annual Book of ASTM Standards*, Vol. 10.02, Designations: D495-84; D618; D2303; and D3638.

Several manufacturers have introduced various electrosurgical instruments which are known to solve many of the aforementioned problems associated with sealing, cutting, cauterizing and/or coagulating differently-sized vessels. Some of these instruments are described in co-pending U.S. patent application Ser. No. 09/178,027 filed on Oct. 23, 1998, entitled OPEN VESSEL SEALING FORCEPS WITH DISPOSABLE ELECTRODES, co-pending U.S. patent application Ser. No. 09/425,696 filed on Oct. 22, 1999, entitled OPEN VESSEL SEALING FORCEPS WITH DISPOSABLE ELECTRODES, co-pending U.S. patent application Ser. No. 09/177,950 filed on Oct. 23, 1998, entitled ENDOSCOPIC BIPOLAR ELECTROSURGICAL FORCEPS; and co-pending U.S. patent application Ser. No. 09/621,029 filed on Jul. 21, 2000, entitled ENDOSCOPIC BIPOLAR ELECTROSURGICAL FORCEPS, the entire contents of all of which are hereby incorporated by reference herein.

However, it has been found that since many electrosurgical instruments are designed for re-use during subsequent operations, repeated use of the electrosurgical instruments after sterilization may result in inconsistent current tracking over the surface of the insulation and/or activation irregularities which can cause flashover. Activation irregularities may also occur on or near the surface of the insulation with disposable and/or partially disposable instruments when the instrument is used beyond its recommended number of activation cycles during the course of the operation.

Thus, a need exists to develop an electrosurgical instrument which can seal vessels and tissue consistently and effectively and which will effectively reduce the incidence of flashover.

SUMMARY

The present disclosure generally relates to an open and/or endoscopic electrosurgical instrument which includes a removable electrode assembly having electrodes which are electrically and thermally isolated from the remainder of the instrument by a unique insulating substrate and/or by a uniquely designed insulating substrate and electrically conductive surface. It is envisioned that both the geometric shape of the insulating substrate (relative to the geometric shape of the electrically conductive surface) and/or the type of insulating material used contribute to the overall reduction of the incidence of flashover.

More particularly, the present disclosure relates to an electrode assembly for use with an electrosurgical instrument which includes opposing end effectors and a handle for effecting movement of the end effectors relative to one another. The assembly includes a housing having at least one portion which is removably engageable with at least one portion of the electrosurgical instrument (e.g., handle, end effector, pivot, shaft, etc.) and a pair of electrodes. Each electrode preferably includes an electrically conductive sealing surface and an insulating substrate and is dimensioned to be selectively engageable with the end effectors such that the electrodes reside in opposing relation relative to one another.

In one embodiment, the dimensions of the insulating substrate are different from the dimensions of the electrically conductive sealing surface which effectively reduces the incidence of flashover.

In another embodiment, the insulating substrate of each of the electrodes includes a mechanical interface for engaging a complimentary mechanical interface disposed on the corresponding end effector of the electrosurgical instrument. For example, the mechanical interface of the substrate may include a detent and the mechanical interface of the corresponding end effector may include a complimentary socket for receiving the detent.

Preferably, the insulating substrate is mounted to the electrically conductive sealing surface by stamping, by overmolding, by overmolding a stamped seal plate and/or by overmolding a metal injection molded seal plate. In another embodiment, the electrically conductive sealing surface includes a pinch trim and the insulating substrate extends beyond the periphery of the electrically conductive sealing surface. All of these manufacturing techniques are contemplated to effectively reduce the incidence of flashover during activation.

In another embodiment of the present disclosure, the insulating substrate is made from a material having a Comparative Tracking Index of about 300 volts to about 600 volts. Preferably, the insulating substrate is substrate is made from a group of materials which include Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenyleneoxide dispersion and Acrylonitrile Styrene Acrylate.

Other embodiments of the present disclosure include a housing having a bifurcated distal end which forms two resilient and flexible prongs which each carry an electrode designed to engage a corresponding end effector. In another embodiment, the end effectors are disposed at an angle ($\alpha$) relative to the distal end of the shaft of the electrosurgical instrument. Preferably, the angle is about fifty degrees to about seventy degrees. The end effectors and, in turn, the electrodes, can also be dimensioned to include a taper along a width "W" (See FIG. 2).

The present disclosure also relates to an electrode assembly for use with an electrosurgical instrument having a handle and at least one shaft for effecting movement of a pair of opposing end effectors relative to one another. The electrode assembly includes a housing which is removably engageable with the shaft and/or the handle and a pair of electrodes. Each electrode is removably engageable with a corresponding end effector and includes an electrically conductive sealing surface with a first geometric shape and an insulating substrate with a second geometric shape. Preferably, the second geometric shape of the insulating substrate is different from the first geometric shape of the sealing surface which effectively reduces the incidence of flashover during activation of the instrument.

Preferably, the electrode assembly is removable, disposable and replaceable after the electrode assembly is used beyond its intended number of activation cycles. Alternatively, the electrode assembly and/or the electrodes may be integrally associated with the end effectors of the instrument and are not removable. In this instance, the electrosurgical instrument (open or endoscopic) may be designed for single use applications and the entire instrument is fully disposable after the surgery is completed.

BRIEF DESCRIPTION OF THE DRAWINGS

FIG. 8A is a perspective view of the forceps of the present disclosure showing the operative motion of the forceps to effect sealing of a tubular vessel;

FIG. 9 is an enlarged, partial perspective view of a sealing site of a tubular vessel;

DETAILED DESCRIPTION

It has been found that by altering the electrode insulating material, surgeons can more readily and easily produce a consistent, high quality seal and reduce the chances of so-called "flashover." Flashover is simply a visual anomaly which occurs during sealing as a result of inconsistent and/or irregular current tracking over the surface of the insulate which may occur when the instrument is repeatably used during surgery. Flashover tends to char the surface of the insulate but is not know to effect seal quality. However, it may effect the life of the instrument.

It is contemplated that one way to reduce the incidence of flashover is to alter the geometry of the insulation relative to the electrically conductive sealing surface which effectively increases the overall distance that the electrical current must travel along the predetermined electrical path. It is also contemplated that manufacturing the insulating substrate from a specific material having certain properties will, likewise, reduce the incidence of flashover.

Figure 1:
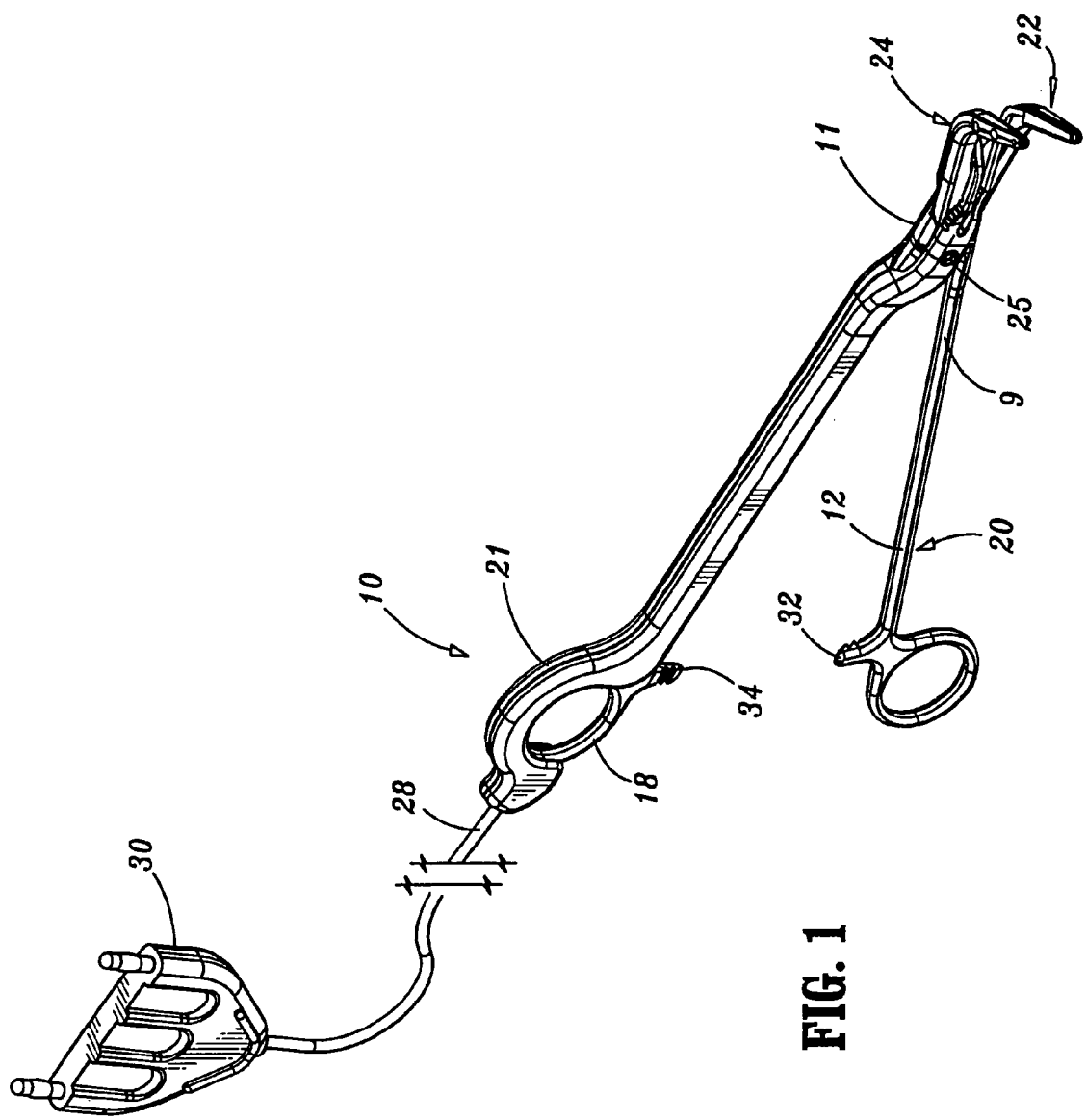
FIG. 1 is a perspective view of an open bipolar forceps according to one embodiment of the present disclosure.
Figure 2:
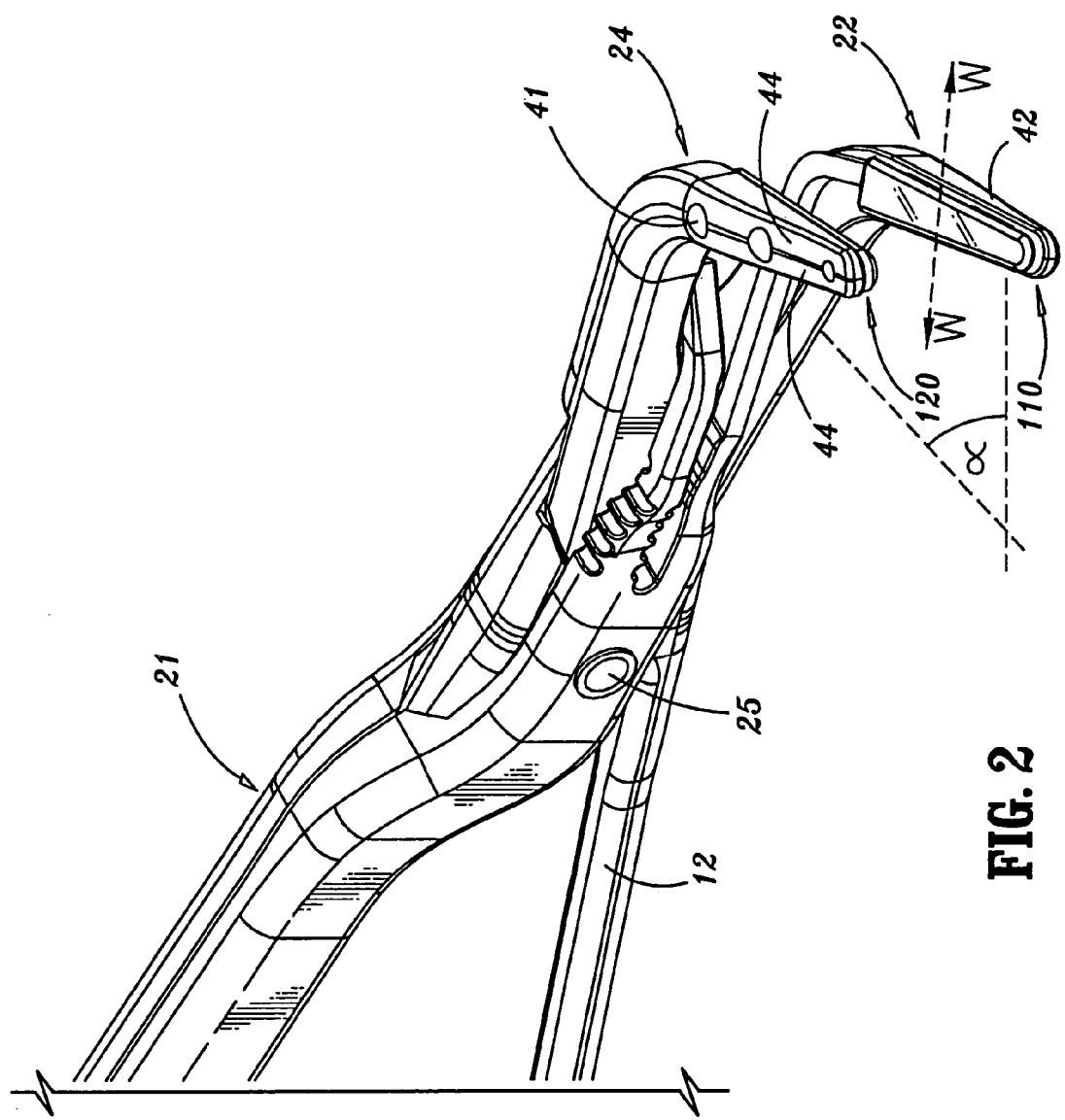
FIG. 2 is an enlarged, perspective view of a distal end of the bipolar forceps shown in FIG. 1.
Figure 3:
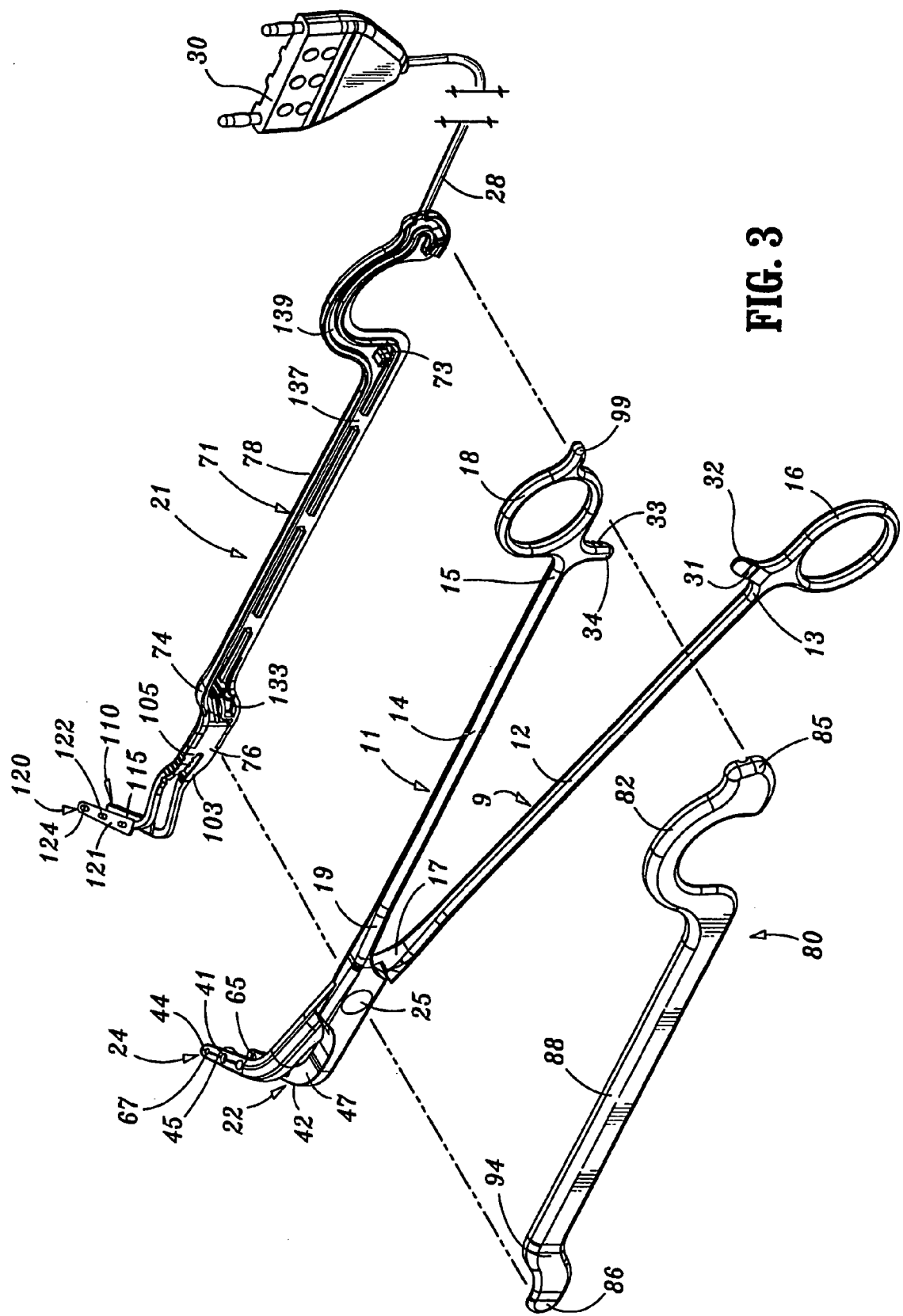
FIG. 3 is a perspective view with parts separated of the forceps shown in FIG. 1.

Referring now to FIGS. 1–3, a bipolar forceps 10 is shown for use with open surgical procedures by way of example and includes a mechanical forceps 20 and a disposable electrode assembly 21. In the drawings and in the description which follows, the term "proximal", as is traditional, will refer to the end of the forceps 10 which is closer to the user, while the term "distal" will refer to the end which is further from the user. In addition, although the majority of the figures, i.e., FIGS. 1–7A and 8A, show one embodiment of the presently described instrument for use with open surgical procedures, e.g., forceps 20, it is envisioned that the same properties as shown and described herein may also be employed with or incorporated on an endoscopic instrument 100 such as the embodiment shown by way of example in FIG. 8B.

FIGS. 1–3 show mechanical forceps 20 which includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto which allows a user to effect movement of at least one of the shaft portions, e.g., 12 relative to the other, e.g., 14. Extending from the distal ends 17 and 19 of each shaft portion 12 and 14 are end effectors 24 and 22, respectively. The end effectors 24 and 22 are movable relative to one another in response to movement of handle members 16 and 18. Preferably, the end effectors 22, 24 (and, in turn, the jaw members 42 and 44 and the corresponding electrodes 110 and 120) are disposed at an angle alpha (α) relative to the distal ends 19, 17 (See FIG. 2). It is contemplated that the angle alpha (α) is in the range of about fifty degrees to about seventy degrees relative to the distal ends 19, 17.

It is envisioned that angling the end effectors 22, 24 at an angle alpha (α) relative to the distal ends 19, 17 may be advantageous for two reasons: 1) the angle of the end effectors, jaw members and electrodes will apply more constant pressure for a constant tissue thickness at parallel; and 2) the thicker proximal portion of the electrode, e.g., 110, (as a result of the taper along width "W") will resist bending due to the reaction force of the tissue 150. The tapered "W" shape (FIG. 2) of the electrode 110 is determined by calculating the mechanical advantage variation from the distal to proximal end of the electrode 110 and adjusting the width of the electrode 110 accordingly. It is contemplated that dimensioning the end effectors 22, 24 at an angle of about 50 degrees to about 70 degrees is preferred for accessing and sealing specific anatomical structures relevant to prostatectomies and cystectomies, e.g., the dorsal vein complex and the lateral pedicles.

Figure 8B:
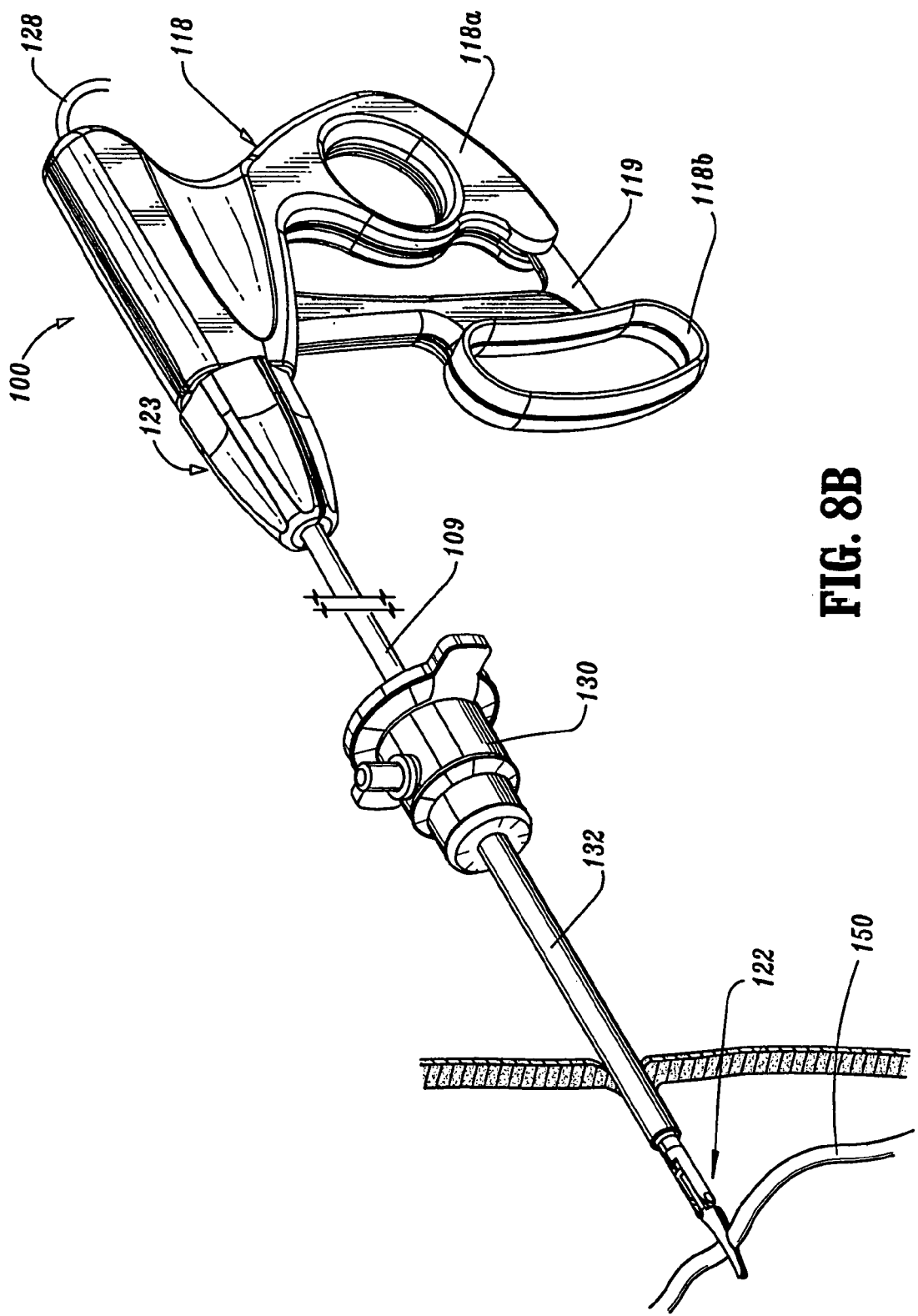
FIG. 8B is a perspective view of an endoscopic version of the present disclosure showing the operative motion of the instrument to effect sealing of a tubular vessel.

Preferably, shaft portions 12 and 14 are affixed to one another at a point proximate the end effectors 24 and 22 about a pivot 25 such that movement of one of the handles 16, 18 will impart relative movement of the end effectors 24 and 22 from an open position wherein the end effectors 22 and 24 are disposed in spaced relation relative to one another to a clamping or closed position wherein the end effectors 22 and 24 cooperate to grasp a tubular vessel 150 therebetween (see FIGS. 8A and 8B). It is envisioned that pivot 25 has a large surface area to resist twisting and movement of forceps 10 during activation. It is also envisioned that the forceps 10 can be designed such that movement of one or both of the handles 16 and 18 will only cause one of the end effectors, e.g., 24, to move with respect to the other end effector, e.g., 22.

As best seen in FIG. 3, end effector 24 includes an upper or first jaw member 44 which has an inner facing surface 45 and a plurality of mechanical interfaces disposed thereon which are dimensioned to releasable engage a portion of a disposable electrode assembly 21 which will be described in greater detail below. Preferably, the mechanical interfaces include sockets 41 which are disposed at least partially through inner facing surface 45 of jaw member 44 and which are dimensioned to receive a complimentary detent 122 attached to upper electrode 120 of the disposable electrode assembly 21. While the term "socket" is used herein, it is contemplated that either a male or female mechanical interface may be used on jaw member 44 with a mating mechanical interface disposed on the disposable electrode assembly 21.

In some cases, it may be preferable to manufacture mechanical interfaces 41 along another side of jaw member 44 to engage a complimentary mechanical interface of the disposable electrode assembly 21 in a different manner, e.g., from the side. Jaw member 44 also includes an aperture 67 disposed at least partially through inner face 45 of end effector 24 which is dimensioned to receive a complimentary guide pin 124 disposed on electrode 120 of the disposable electrode assembly 21.

End effector 22 includes a second or lower jaw member 42 which has an inner facing surface 47 which opposes inner facing surface 45. Preferably, jaw members 42 and 44 are dimensioned generally symmetrically, however, in some cases it may be preferable to manufacture the two jaw members 42 and 44 asymmetrically depending upon a particular purpose. In much the same fashion as described above with respect to jaw member 44, jaw member 42 also includes a plurality of mechanical interfaces or sockets 43 disposed thereon which are dimensioned to releasable engage a complimentary portion disposed on electrode 110 of the disposable electrode assembly 21 as described below. Likewise, jaw member 42 also includes an aperture 65 disposed at least partially through inner face 47 which is dimensioned to receive a complimentary guide pin 127 (see FIG. 4) disposed on electrode 110 of the disposable electrode assembly 21.

Preferably, shaft members 12 and 14 of the mechanical forceps 20 are designed to transmit a particular desired force to the opposing inner facing surfaces of the of the jaw members 22 and 24, respectively, when clamped. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34, respectively. Preferably, each ratchet, e.g., 32, extends from the proximal end 13 of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. Preferably, each ratchet position holds a specific, i.e., constant, strain energy in the shaft members 12 and 14 which, in turn, transmits a specific force to the end effectors 22 and 24 and, thus, the electrodes 120 and 110.

In some cases it may be preferable to include other mechanisms to control and/or limit the movement of the jaw members 42 and 44 relative to one another. For example, a ratchet and pawl system could be utilized to segment the movement of the two handles into discrete units which will, in turn, impart discrete movement to the jaw members 42 and 44 relative to one another.

Preferably, at least one of the shaft members, e.g., 14, includes a tang 99 which facilitates manipulation of the forceps 20 during surgical conditions as well as facilitates attachment of electrode assembly 21 on mechanical forceps 20 as will be described in greater detail below.

Figure 5:
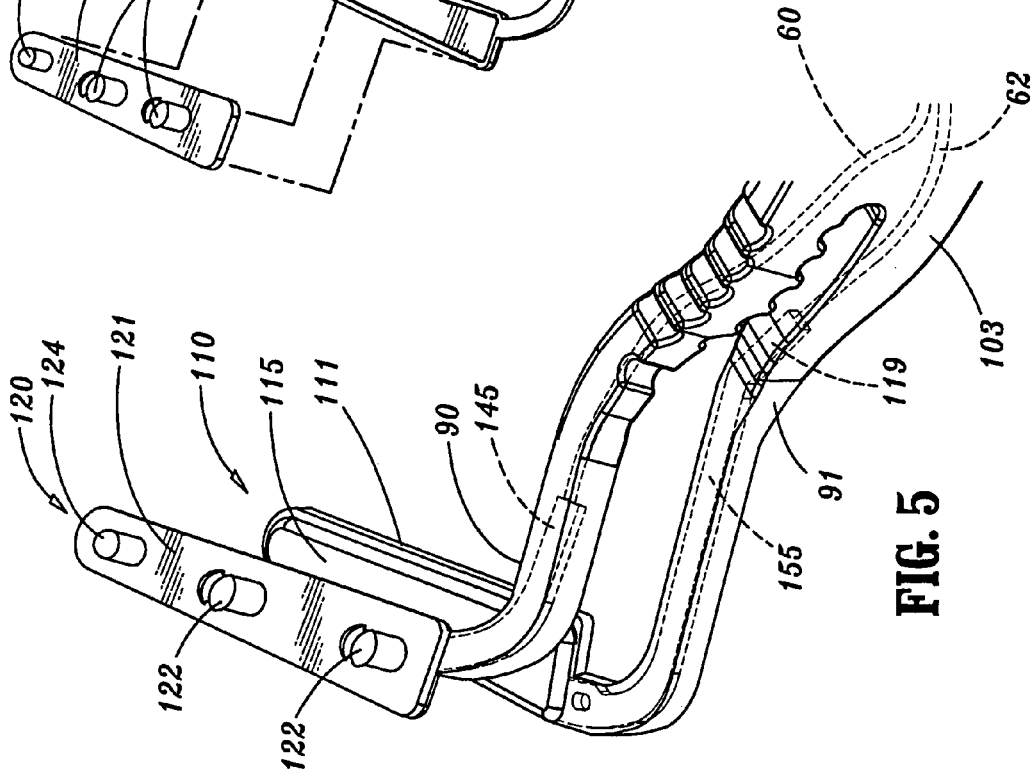
FIG. 5 is an enlarged, perspective view of a distal end of the electrode assembly of FIG. 4.

As best seen in FIGS. 2, 3 and 5, disposable electrode assembly 21 is designed to work in combination with mechanical forceps 20. Preferably, electrode assembly 21 includes housing 71 which has a proximal end 77, a distal end 76 and an elongated shaft plate 78 disposed therebetween. A handle plate 72 is disposed near the proximal end 77 of housing 71 and is sufficiently dimensioned to releasably engage and/or encompass handle 18 of mechanical forceps 20. Likewise, shaft plate 78 is dimensioned to encompass and/or releasably engage shaft 14 and pivot plate 74 disposed near the distal end 76 of housing 71 and is dimensioned to encompass pivot 25 and at least a portion of distal end 19 of mechanical forceps 20. It is contemplated that the electrode assembly 21 can be manufactured to engage either the first or second members 9 and 11 of the mechanical forceps 20 and its respective component parts 12, 16 or 14, 18, respectively.

In the embodiment shown in FIG. 3, handle 18, shaft 14, pivot 25 and a portion of distal end 19 are all dimensioned to fit into corresponding channels located in housing 71. For example, a channel 139 is dimensioned to receive handle 18, a channel 137 is dimensioned to receive shaft 14 and a channel 133 is dimensioned to receive pivot 25 and a portion of distal end 19.

Electrode assembly 21 also includes a cover plate 80 which is also designed to encompass and/or engage mechanical forceps 20 in a similar manner as described with respect to the housing 71. More particularly, cover plate 80 includes a proximal end 85, a distal end 86 and an elongated shaft plate 88 disposed therebetween. A handle plate 82 is disposed near the proximal end 85 and is preferably dimensioned to releasable engage and/or encompass handle 18 of mechanical forceps 20. Likewise, shaft plate 88 is dimensioned to encompass and/or releasable engage shaft 14 and a pivot plate 94 disposed near distal end 86 is designed to encompass pivot 25 and distal end 19 of mechanical forceps 20. Preferably, handle 18, shaft 14, pivot 25 and distal end 19 are all dimensioned to fit into corresponding channels (not shown) located in cover plate 80 in a similar manner as described above with respect to the housing 71.

Figure 4:
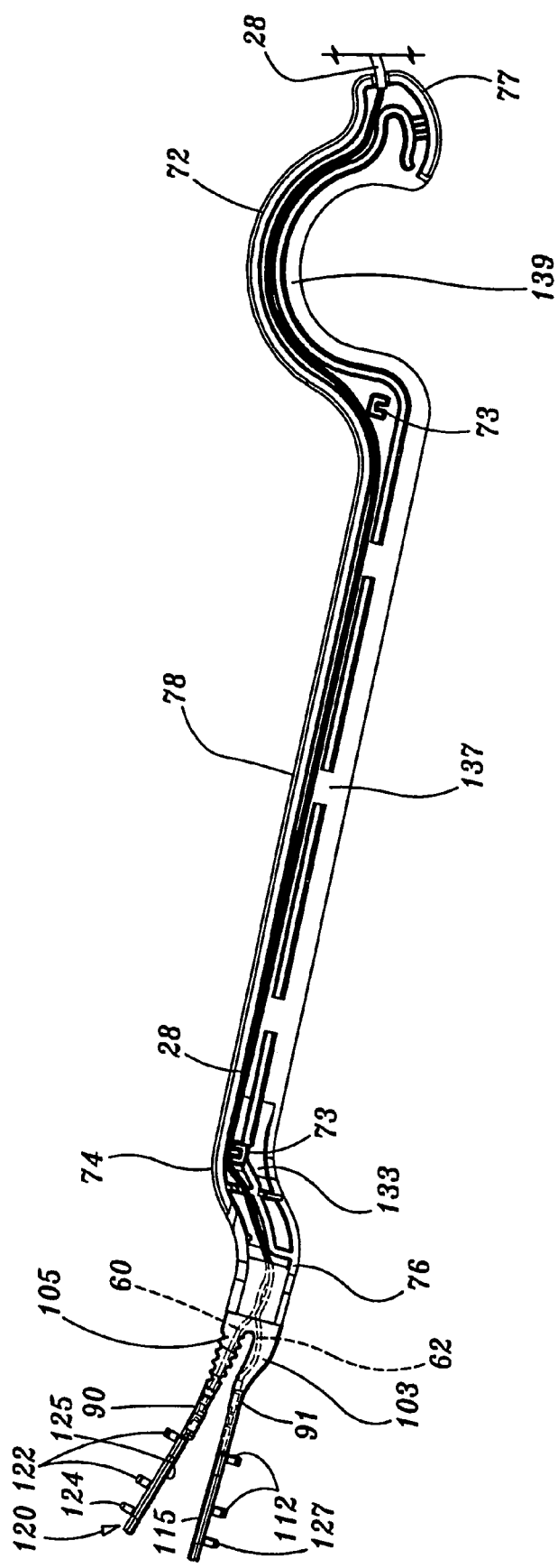
FIG. 4 is an enlarged, side view of an electrode assembly of FIG. 1 shown without a cover plate.
Figure 7A:
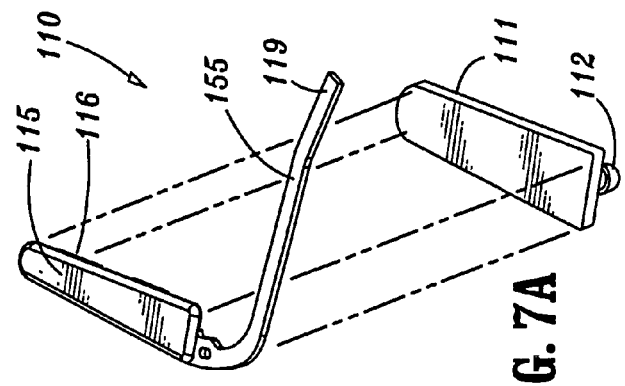
FIG. 7A is a perspective view with parts separated of a lower electrode of the electrode assembly of FIG. 5.

As best seen with respect to FIGS. 3 and 4, housing 71 and cover plate 80 are designed to engage one another over first member, e.g., 11, of mechanical forceps 20 such that first member 11 and its respective component parts, e.g., handle 18, shaft 14, distal end 19 and pivot 25, are disposed therebetween. Preferably, housing 71 and cover plate 80 include a plurality of mechanical interfaces disposed at various positions along the interior of housing 71 and cover plate 80 to effect mechanical engagement with one another. More particularly, a plurality of sockets 73 are disposed proximate handle plate 72, shaft plate 78 and pivot plate 74 of housing 71 and are dimensioned to releasably engage a corresponding plurality of detents (not shown) extending from cover plate 80. It is envisioned that either male or female mechanical interfaces or a combination of mechanical interfaces may be disposed within housing 71 with mating mechanical interfaces disposed on or within cover plate 80.

As best seen with respect to FIGS. 5–7A, the distal end 76 of electrode assembly 21 is bifurcated such that two prong-like members 103 and 105 extend outwardly therefrom to support electrodes 110 and 120, respectively. More particularly, electrode 120 is affixed at an end 90 of prong 105 and electrode 110 is affixed at an end 91 of prong 103. It is envisioned that the electrodes 110 and 120 can be affixed to the ends 91 and 90 in any known manner, e.g., friction-fit, snap-fit engagement, crimping, etc. Moreover, it is contemplated that the electrodes 110 and 120 may be selectively removable from ends 90 and 91 depending upon a particular purpose and/or to facilitate assembly of the electrode assembly 21.

A pair of wires 60 and 62 are connected to the electrodes 120 and 110, respectively, as best seen in FIGS. 4 and 5. Preferably, wires 60 and 62 are bundled together and form a wire bundle 28 (FIG. 4) which runs from a terminal connector 30 (see FIG. 3), to the proximal end 77 of housing 71, along the interior of housing 71, to distal end 76. Wire bundle 28 is separated into wires 60 and 62 proximate distal end 76 and the wires 60 and 62 are connected to each electrode 120 and 110, respectively. In some cases it may be preferable to capture the wires 60 and 62 or the wire bundle 28 at various pinch points along the inner cavity of the electrode assembly 21 and enclose the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases it may be preferable to extend wires 60 and 62 to an electrosurgical generator (not shown).

Figure 6:
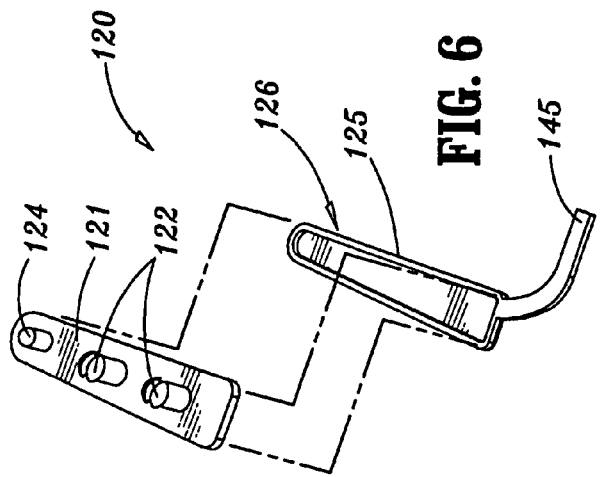
FIG. 6 is a perspective view with parts separated of an upper electrode of the electrode assembly of FIG. 5.

As best seen in FIG. 6, electrode 120 includes an electrically conductive seal surface 126 and an electrically insulative substrate 121 which are attached to one another by snap-fit engagement or some other method of assembly, e.g., overmolding of a stamping or metal injection molding. Preferably, substrate 121 is made from molded plastic material and is shaped to mechanically engage a corresponding socket 41 located in jaw member 44 of end effector 24 (see FIG. 2). The substrate 121 not only insulates the electric current but it also aligns electrode 120 both of which contribute to the seal quality, consistency and the reduction of flashover.

Figure 7B:
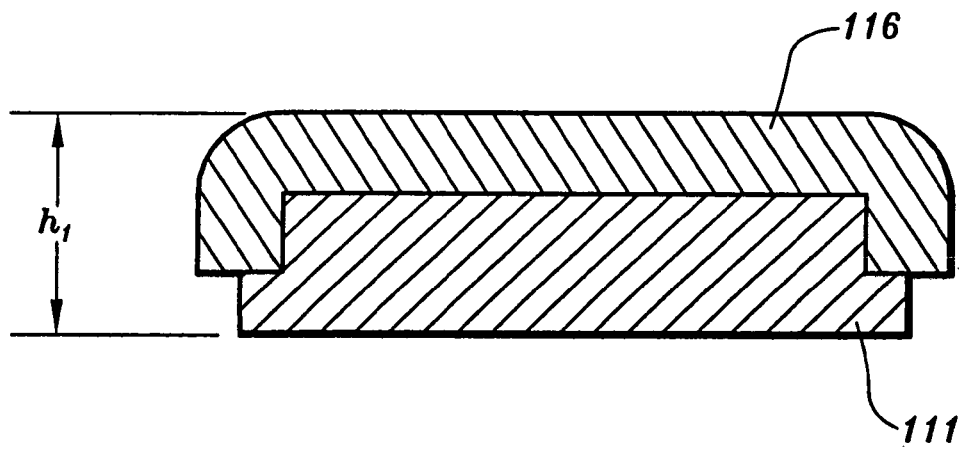
FIG. 7B is a cross section of a prior art electrode configuration with the electrode extending over the sides of the insulator.
Figure 7C:
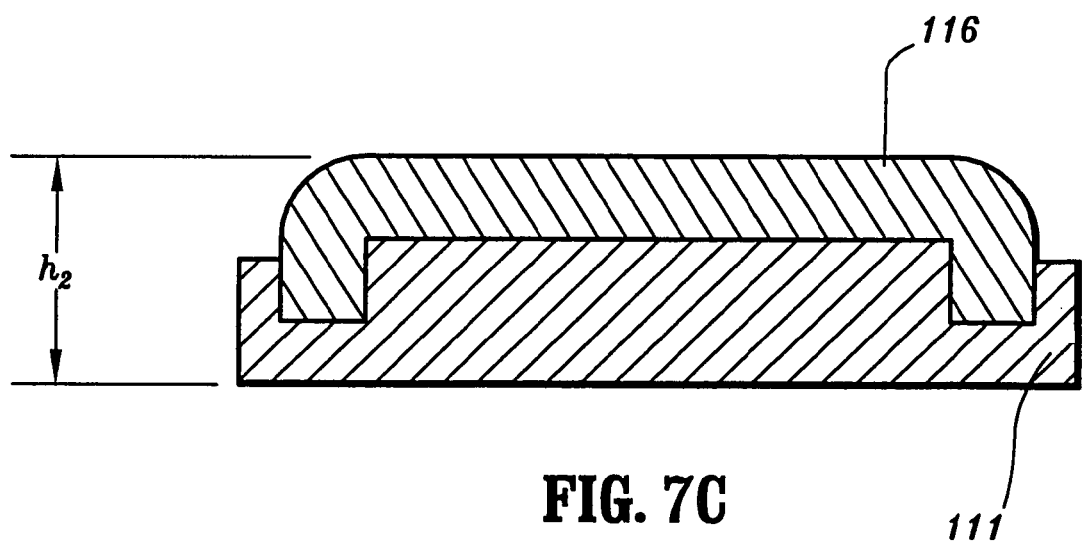
FIG. 7C is a cross section of an electrode with the insulator extending beyond the sides of the electrode.

Moreover, by attaching the conductive surface 126 to the substrate 121 utilizing one of the above assembly techniques, the alignment and thickness, i.e., height "h2", of the electrode 120 can be controlled. For example and as best illustrated in the comparison of FIGS. 7B and 7C, the overmolding manufacturing technique reduces the overall height "h2" (FIG. 7C) of the electrode 120 compared to traditional manufacturing techniques which yield a height of "h1" (FIG. 7B). The smaller height "h2" allows a user access to smaller areas within the body and facilitates sealing around more delicate tissue areas. Moreover, it is contemplated that the overmolding technique provides more insulation along the side of the electrically conductive surface which also effectively reduces the incidence of flashover.

Preferably, substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44. A slide-fit technique is also contemplated such as the slide-fit technique describe with respect to commonly-assigned, co-pending PCT Application Serial No. PCT/US01/11218, by Tetzlaff et al., the entire contents of which is hereby incorporated by reference herein.

Conductive seal surface 126 includes a wire crimp 145 designed to engage the distal end 90 of prong 105 of electrode assembly 21 and electrically engage a corresponding wire connector affixed to wire 60 located within electrode assembly. Seal surface 126 also includes an opposing face 125 which is designed to conduct an electrosurgical current to a tubular vessel or tissue 150 when it is held thereagainst.

Electrode 110 includes similar elements and materials for insulating and conducting electrosurgical current to tissue 150. More particularly, electrode 110 includes an electrically conductive seal surface 116 and an electrically insulative substrate 111 which are attached to one another by one of the above methods of assembly. Substrate 111 includes a plurality of detents 112 which are dimensioned to engage a corresponding plurality of sockets 43 and aperture 65 located in jaw member 42. Conductive seal surface 116 includes an extension 155 having a wire crimp 119 which engages the distal end 91 of prong 103 and electrically engages a corresponding wire connector affixed to wire 62 located in housing 71. Seal surface 116 also includes an opposing face 115 which conducts an electrosurgical current to a tubular vessel or tissue 150 when it is held thereagainst. It is contemplated that electrodes 110 and 120 can be formed as one piece and include similar components and/or dimensions for insulating and conducting electrical energy in a manner to reduce the incidence of flashover.

As mentioned above, it is envisioned that flashover may be reduced and/or eliminated by altering the physical or chemical characteristics of the insulator and electrode, e.g., by altering the geometry/shape of the insulator, by changing the type of material used to manufacture the insulator and/or by coating the insulator with different materials. Modifying the geometry of the insulator 111 and/or conductive surface 116 creates a longer path of the current to travel over the insulator 111 before flashover occurs. For example and as best shown in the comparison of FIG. 7B (prior art) with newly disclosed FIGS. 7C and 7D, substrates 111, 121 are designed to extend along width "W" (FIG. 2) such that the width of the insulating substrate, e.g., 111, exceeds the width of the electrically conductive seal surface 116. It is envisioned that manufacturing these electrically conductive sealing surface 116 and insulator 111 configurations may be accomplished by various manufacturing techniques such as overmolding of a stamping and/or metal injection molding.

Stamping is defined herein to encompass virtually any press operation known in the trade, including, but not limited to: blanking, shearing, hot or cold forming, drawing, bending and coining.

Figure 7D:
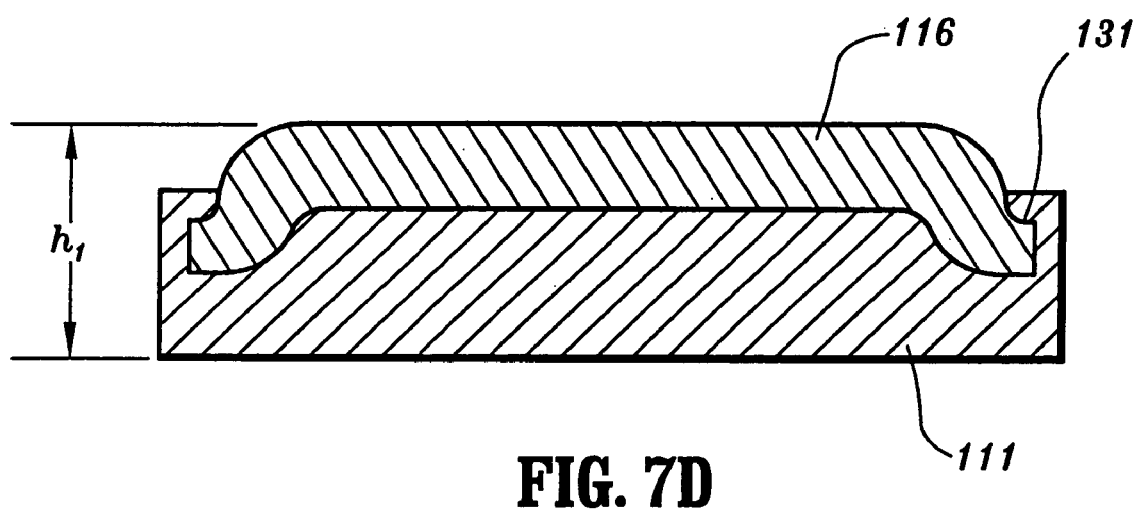
FIG. 7D is a cross section of an overmolded stamped electrode configuration showing the insulator capturing a pinch trim which depends from the electrically conductive surface.

As best seen in FIG. 7D, the electrically conductive sealing surface 116 may include a pinch trim 131 which facilitates secure integral engagement of the insulate and the electrically conductive sealing surface 116 during the assembly and/or manufacturing process. It is envisioned that manufacturing the electrodes 110 and 120 in this fashion will reduce the incidence of flashover. Other manufacturing techniques may also be employed to achieve similar electrically conductive sealing surface 116 and insulator 111 configurations which will effectively the incidence of flashover.

Although it is contemplated that geometric modification of the insulator 111 relative to the electrically conductive sealing surface 116 reduces the incidence of flashover, in some cases it may be preferable to simply utilize a different material for the insulator to reduce flashover. For example it is known that all plastics have a different resistance to flashover which is commonly measured using a Comparative Tracking Index (CTI). The CTI value required to resist flashover is typically dictated in part by the maximum voltage of the vessel sealing generator, however, other parameters such as frequency also typically effect flashover.

It has been found that in lieu of changing the geometry of the insulator 111 and/or conductive surface 116, a plastic insulation can be employed having a CTI value of about 300 to about 600 volts. Examples of high CTI materials include nylons and syndiotactic polystryrenes such as QUESTRA® manufactured by DOW Chemical. Other materials may also be utilized either alone or in combination to reduce flashover, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamideimide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

In some cases, however, it may be preferable to alter both the geometry of the insulator 111 and/or conductive surface 116 and/or utilize a plastic insulation that does not have a CTI value of about 300 to about 600 volts. Alternatively, certain coatings can be utilized either alone or in combination with one of the above manufacturing techniques to reduce flashover.

Figure 10:
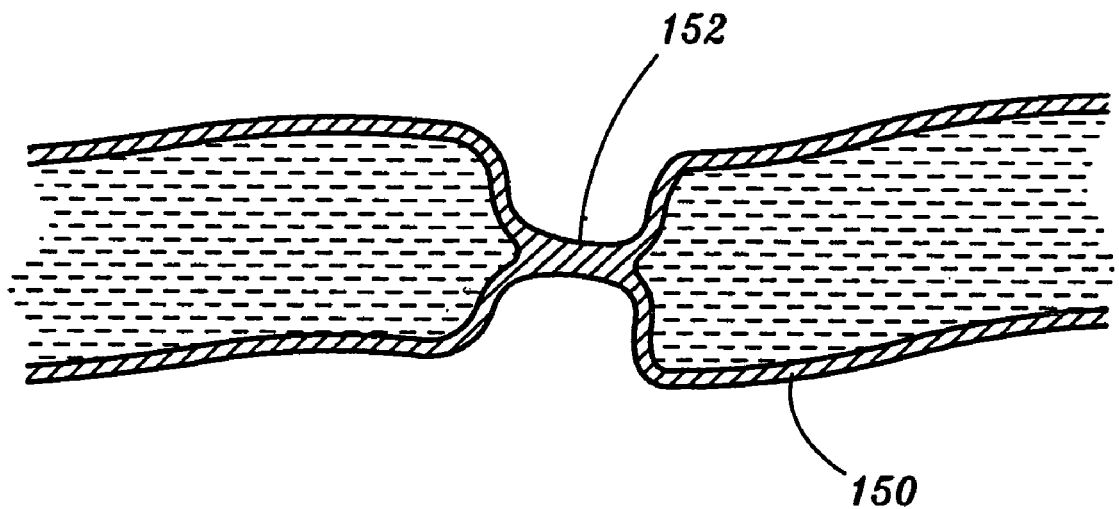
FIG. 10 is a longitudinal cross-section of the sealing site taken along line 10—10 of FIG. 9.

FIG. 8A shows the bipolar forceps 10 during use wherein the handle members 16 and 18 are moved closer to one another to apply clamping force to the tubular tissue 150 to effect a seal 152 as shown in FIGS. 9 and 10. Once sealed, the tubular vessel 150 can be cut along seal 152 to separate the tissue 150 and form a gap 154 therebetween as shown in FIG. 11.

After the bipolar forceps 10 is used or if the electrode assembly 21 is damaged, the electrode assembly 21 can be easily removed and/or replaced and a new electrode assembly 21 may be attached to the forceps in a similar manner as described above. It is envisioned that by making the electrode assembly 21 disposable, the electrode assembly 21 is less likely to become damaged since it is only intended for a single operation and, therefore, does not require cleaning or sterilization. As a result, the functionality and consistency of the sealing components, e.g., the conductive surfaces 126, 116 and insulating surfaces 121, 111 will assure a uniform and quality seal. Alternatively, the entire electrosurgical instrument may be disposable which, again, will assure a uniform and quality seal with minimal flashover effect.

Figure 11:
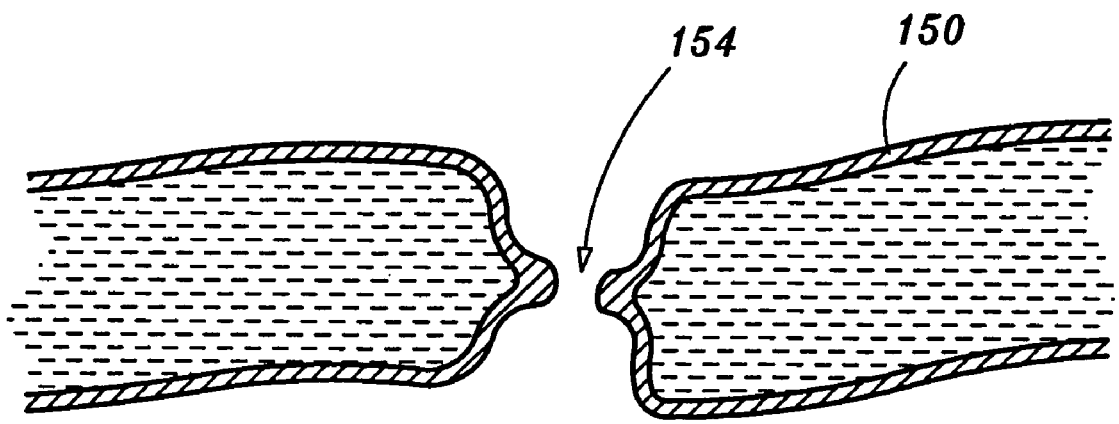
FIG. 11 is a longitudinal cross-section of the sealing site of FIG. 9 after separation of the tubular vessel.

FIG. 8B shows an endoscopic bipolar instrument 100 during use wherein movement of a handle assembly 128 applies clamping force on the tubular tissue 150 to effect a seal 152 as shown in FIGS. 9–11. As shown, a shaft 109 and the electrode assembly 122 are inserted through a trocar 130 and cannula 132 and a handle assembly 118 is actuated to cause opposing jaw members of the electrode assembly 122 to grasp tubular vessel 150 therebetween. More particularly, a movable handle 118b is moved progressively towards a fixed handle 118a which, in turn, causes relative movement of the jaw members from an open, spaced-apart position to a closed, sealing position. A rotating member 123 allows the user to rotate the electrode assembly 122 into position about the tubular tissue 150 prior to activation.

After the jaw members are closed about the tissue 150, the user then applies electrosurgical energy via connection 128 to the tissue 150. By controlling the intensity, frequency and duration of the electrosurgical energy applied to the tissue 150, the user can either cauterize, coagulate/desiccate seal and/or simply reduce or slow bleeding.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16 and 18 is required to deflect the electrodes in the same plane. It is envisioned that this could improve seal quality and consistency.

Although it is preferable that the electrode assembly 21 include housing 71 and cover plate 80 to engage mechanical forceps 20 therebetween, in some cases it may be preferable to manufacture the electrode assembly 21 such that only one piece, e.g., housing 71 is required to engage mechanical forceps 20.

It is envisioned that the outer surface of the end effectors may include a nickel-based material, coating, stamping, metal injection molding which is designed to reduce adhesion between the end effectors (or components thereof) with the surrounding tissue during or after sealing.

Alternatively, certain of the above-mentioned coatings can be utilized either alone or in combination with one of the above manufacturing techniques to supplement overall thermal spread reduction. These effects are discussed in detail in concurrently-filed, co-pending, commonly assigned PCT Application Serial No. PCT/US01/11412 entitled "ELECTROSURGICAL INSTRUMENT WHICH REDUCES COLLATERAL DAMAGE TO ADJACENT TISSUE" by Johnson et al.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A system comprising an electrode assembly and an electrosurgical instrument having opposing end effectors and a handle which effect movement of the end effectors relative to one another, the electrode assembly comprising:
  a housing having at least one portion which removably engages at least one portion of the electrosurgical instrument;
  a pair of electrodes each including an electrically conductive sealing surface and an insulating substrate, the electrodes being removably engageable with and selectively separable and replaceable from the end effectors of the electrosurgical instrument such that the electrodes reside in opposing relation relative to one another; wherein the insulating substrate is made from a material having a Comparative Tracking Index of about 300 volts to about 600 volts to reduce the incidence of flashover.

2. The system according to claim 1 wherein the insulating substrate is selected from the group consisting of nylon, syndiotactic-polystryrene, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenylene-oxide dispersion and acrylonitrile styrene acrylate.

3. The system according to claim 1 wherein the dimensions of the insulating substrate differ from the dimensions of the electrically conductive sealing surface to reduce the incidence of flashover.

4. The system according to claim 1, wherein said insulating substrate is mounted to the electrically conductive sealing surface by an overmolded stamped seal plate material.

5. The system according to claim 1, wherein said insulating substrate is mounted to the electrically conductive sealing surface by an overmolded metal injection molded seal plate material.

6. The system according to claim 1 wherein the electrode assembly is disposable.

7. The system according to claim 6 wherein the insulating substrate of each of the electrodes includes at least one mechanical interface for engaging a complementary mechanical interface disposed on the corresponding end effector of the instrument.

8. The system according to claim 7 wherein the mechanical interface of at least one of the substrates includes at least one complementary and the mechanical interface of the corresponding end effector includes at least one complementary socket for receiving the detent.

9. The system according to claim 1 wherein the housing includes a bifurcated distal end which forms two prongs and each electrode is removably attachable to one of the prongs.

10. The system according to claim 1 further comprising at least one ratchet which engages a complementary mechanical interface to maintain a desired closure force between opposing electrodes.

11. The system according to claim 1 wherein at least one of the opposing end effectors and the electrodes is tapered.

12. The system according to claim 1 wherein the end effectors are disposed at an angle relative to a shaft of the electrosurgical instrument.

13. The system according to claim 12 wherein the angle is about sixty degrees to about seventy degrees.

14. The system according to claim 1 wherein the electrically conductive sealing surface of at least one electrode includes a pinch trim and the insulating substrate extends beyond a periphery of the electrically conductive sealing surface.

15. A system comprising an electrode assembly and an electrosurgical instrument having a handle and at least one shaft which effects movement of a pair of opposing end effectors relative to one another, the electrode assembly comprising:
  a housing having at least one portion which removably engages with at least one of a handle and a shaft of the electrosurgical instrument;
  a pair of electrodes each having an electrically conductive sealing surface having a first geometric shape and an insulating substrate having a second geometric shape, the electrodes being removably engageable in a snap-fit manner with the end effectors of the instrument such that the electrodes reside in opposing relation relative to one another; and wherein the second geometric shape of the insulating substrate is different from the first geometric shape of the sealing surface to reduce the incidence of flashover; and
  wherein the pair of electrodes are configured to be selectively engageable, separable and replaceable from the end effectors of the instrument without damaging the end effectors.

16. The system according to claim 15 wherein the electrically conductive sealing surface of at least one electrode includes a pinch trim and the insulating substrate extends beyond a periphery of the electrically conductive sealing surface.

17. The system according to claim 16 wherein the insulating substrate is made from a material having a Comparative Tracking Index of about 300 volts to about 600 volts.

18. A system comprising an electrode assembly and an electrosurgical instrument having opposing end effectors and a handle which effect movement of the end effectors relative to one another, the electrode assembly comprising:
  a housing having at least one portion which removably engages at least one portion of the electrosurgical instrument;
  a pair of electrodes each including an electrically conductive sealing surface and an insulating substrate, the electrodes being removably engageable and selectively separable and replaceable from the end effectors of the instrument such that the electrodes reside in opposing relation relative to one another;
  wherein the insulating substrate is made from a material having a Comparative Tracking Index of about 300 volts to about 600 volts to reduce the incidence of flashover; and
  wherein the pair of electrodes are engageable with the end effectors in at least one of a removable fit arrangement, a snap fit arrangement, a friction fit arrangement, and a crimping fit arrangement.

* * * * *